United States Patent [19]

Uchigaki et al.

[11] Patent Number: 4,512,348

[45] Date of Patent: Apr. 23, 1985

[54] DEVICE FOR AUTOMATICALLY AND CONTINUOUSLY MEASURING THE CONSTITUENT PARTS OF BLOOD

[75] Inventors: Takatoshi Uchigaki; Akio Saito, both of Kyoto; Naoki Yamada, Joyo, all of Japan

[73] Assignee: Kabushiki Kaisha Kyoto Daiichi Kagaku, Japan

[21] Appl. No.: 371,482

[22] Filed: Apr. 23, 1982

[30] Foreign Application Priority Data

Apr. 24, 1981 [JP] Japan ............................... 56-063160
Oct. 9, 1981 [JP] Japan ........................... 56-150924[U]

[51] Int. Cl.$^3$ ........................................... G01N 21/26
[52] U.S. Cl. ..................................... 128/632; 422/81; 73/61 R
[58] Field of Search ............... 128/630, 632, 637, 760; 436/95; 422/64, 67, 81; 73/1 R

[56] References Cited

U.S. PATENT DOCUMENTS

| | | | |
|---|---|---|---|
| 3,449,959 | 6/1969 | Grimshaw | 422/64 X |
| 3,634,868 | 1/1972 | Pelavin et al. | 73/1 R X |
| 3,648,160 | 3/1972 | Beaver | 73/61 R X |
| 4,109,505 | 8/1978 | Clark et al. | 73/1 R |
| 4,119,406 | 10/1978 | Clemens | 128/632 X |
| 4,204,430 | 5/1980 | Tamm et al. | 73/1 R X |
| 4,263,406 | 4/1981 | Bostick et al. | 422/81 X |

Primary Examiner—Edward M. Coven
Attorney, Agent, or Firm—Darby & Darby

[57] ABSTRACT

At the time of drawing the blood continuously from the vein of the patient by means of a catheter and measuring the concentration of a specified constituent part contained in the blood automatically and continuously for long hours, the sample liquid and two sorts of correcting liquids (standard liquid I and base liquid) are sucked by a single sampling nozzle in prescribed order and are supplied to the measuring section through a common channel. Each of the liquids are diluted with a buffer solution at the identical rate with the manifold in the measuring section, are separated from one another through the interposition of air layers among them, and supplied to a sensor. The outputs of the measured sample liquid from the sensor are corrected by the outputs of each of the neighboring measured correcting liquids in succession and are displayed as measured values. In the blood-drawing section, there is used a double-current catheter having the first and second catheter arrangements which are constructed so as to be incorporated directly into the tube pump.

6 Claims, 16 Drawing Figures

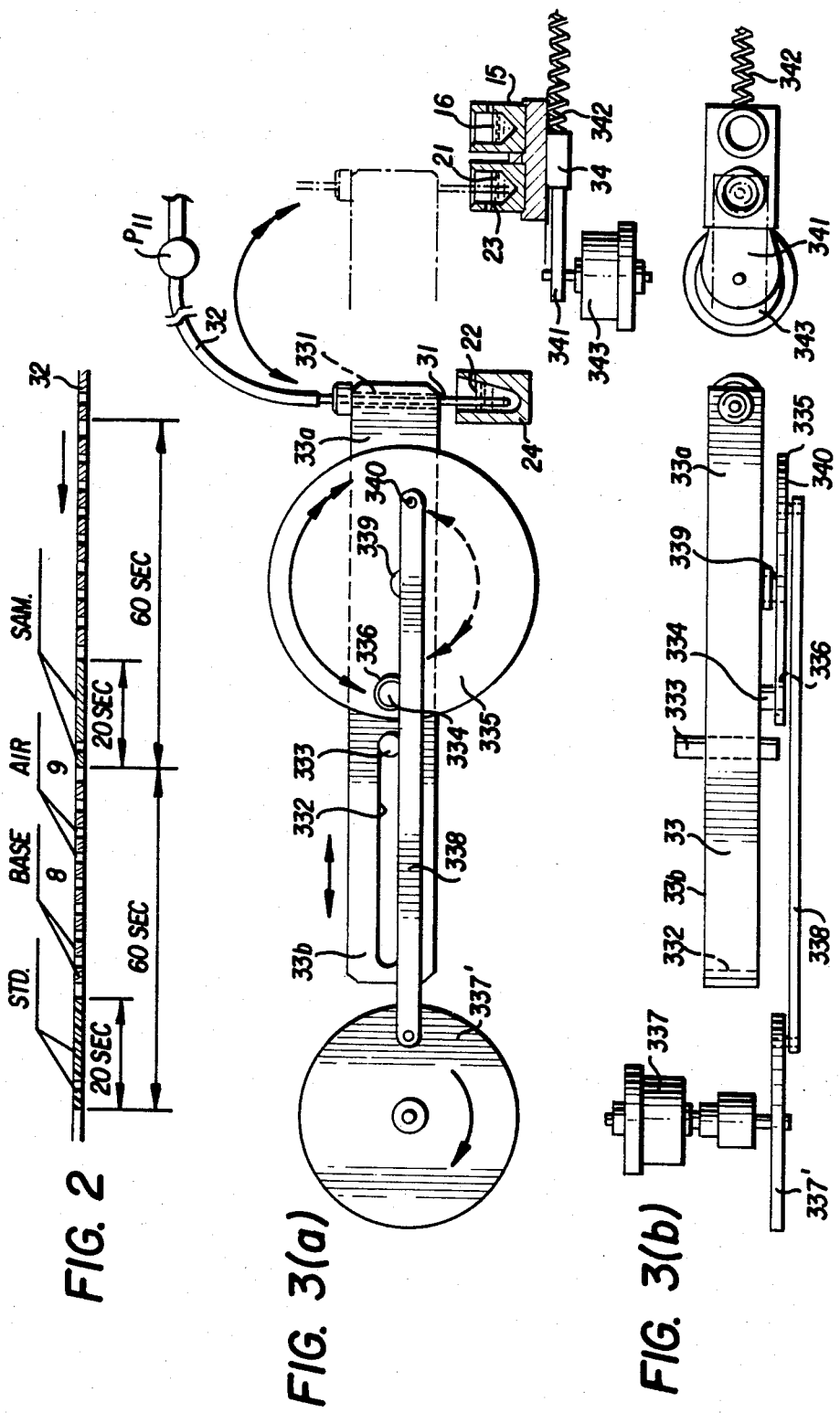

DEVICE FOR AUTOMATICALLY AND CONTINUOUSLY MEASURING THE CONSTITUENT PARTS OF BLOOD

STATEMENT OF PRIOR ART (1) Japanese Patent Disclosure No. 52-135795 of 1977 (Japanese patent application No. 52-50886 of 1977) (U.S. patent application Ser. No. 683,806)

A device for correcting a sensor for use in detecting and measuring a desired property, for example, the glucose content, of a liquid sample, wherein a channel extending to the sensor is provided with a channel-switching means, to which are connected a continuously flowing sample source and a reference liquid source being used at the time of making the correction. The continuous measurement is normally made white flowing the sample liquid to the sensor section. In correcting the sensor, the channel from the reference liquid sourse is set OPEN, when the reference liquid is let to flow toward the sensor, while the sample liquid is made to deviate from its ordinary passage and is discharged into the drain section without passing through the sensor section.

For the purpose of detecting the actual dilution ratio of the blood sample which is drawn from the catheter and is diluted with the anticoagulant and the buffer solution, a certain sample for correction use is prepared by diluting at a diffinite dilution ratio a separately picked liquid being regarded as same with or equal to the sample liquid, and the measured value being read from the above-mentioned sample for correction use, which is made to flow from the channel for correction use directly to the sensor, is compared with the measured value of the sample liquid being read at the time of being made to flow from the catheter, whereby the actual dilution ratio is grasped.

BACKGROUND OF THE INVENTION

This invention relates to a device for continuously and automatically monitoring the concentration of specified constituents contained in the blood.

More specifically, this invention provides a measuring device not affected either by the change in the quantity of flow passing through the tube which forms the measuring channel or by the drift of the detector at the time of continuously sampling the blood from the blood-vessel of the patient by means of a catheter in order to measure the concentration of a specified constituent of the blood. It further contemplates providing a measuring device in which any mixing ratio of the anticoagulant to the blood can be easily established by using the catheter also having the character of a pump tube when the blood drawing is conducted while supplying the anticoagulant, and which is equipped also with a blood-drawing contrivance of such a kind by the use of which the mixing ratio will remain unchanged even if catheters of "throwaway" type would be replaced one by another in consecutive order.

It must be noted that description will be directed in the following specially to the glucose in the blood, namely, the blood sugar, but it goes without saying that the use of the device according to the invention is not limited only to the blood sugar.

In recent years, a of device that has ability of drawing the blood by a slight amount from a vein of the patient in succession for long hours in order to continuously measure the value of blood sugar has been developed. This device is to be used in the measurement of the pattern of fluctuation in the value of blood sugar while every kind of load test is being performed, or in combination with the bedside monitor of the serious case of diabetes, or joining with the monitor of the blood sugar during and after the operation conducted on the diabetic invalid.

The device of this type is such a one on which the blood is drawn from the living body while being diluted with the anticoagulant by inserting the double-current catheter with an anticoagulant-infusing port and a blood-drawing port into a canula whose pointed head is being held in a vein, and the blood thus drawn is sent to the sensor by a suitable pumping means. In time of correcting the sensor, the double-current catheter is first removed from the canula, and after the correction is completed by the use of a solution of a known concentration, it is connected to the canula again in order to continue the measurement. This system, however, not only is a little too complicated to operate, but also it has a defect that the blood is liable to coagulate within the canula at the time of correcting the sensor.

With the purpose of avoiding such a defect, Japanese Patent Disclosure No. 52-135795 of 1977 U.S. Pat. No. 4,119,406 proposed the provision of a channel-switching means at the channel leading to the sensor.

In the channel-switching means referred-to, which is connected to the continuously flowing sample liquid source and the reference liquid source to be used at the time of correction, the measurement is usually made in succession while letting the sample liquid flow to the sensor section. On the other hand, when the correction of the sensor is to be performed, the channel coming from the reference liquid source is made open in order to let the reference liquid flow into the sensor, while the sample is made to turn its course away so as not to pass through the sensor section but to flow into the drain section. In this way, there is no longer necessity for detaching the catheter even at the time of correcting the sensor, and it is also possible at the same time to avoid the defect that the blood is liable to coagulate.

As for the reference liquid, which is for use in correcting the sensor so that the proper value of concentration may be indicated when the sample secures a definite dilution ratio, it has in practice a tendency to bring about errors in measurement in view of the fact that the dilution ratio may be a little off the established value under the influence of a delicate deformation, for instance, of the channel(tube) if being left intact, so that, in order to hold the tendency mentioned above in check and to detect the actual dilution ratio attributable to the anticoagulant and buffer solution contained in the blood sample which has been withdrawn from the catheter, the prior art referred-to here adopted such a method as comprising the steps of: first picking separately the liquid which is regarded as identical with or equal to the above blood sample, next preparing one sample to be used for the correction by diluting the liquid thus picked at a fixed dilution ratio, then reading the measured value of the sample thus prepared while letting it flow from the channel(tube) for the correction directly to the sensor, and lastly obtaining the actual dilution ratio by comparing the measured value thus obtained wih another measured value having been read when the first sample was allowed to flow from the catheter.

Nevertheless, this prior art (Japanese patent application, No. 52-135795 of 1977) still involves a weak point that must be resolved, as described below, which arises from the fact that the sample source and the reference liquid source are designed in such a manner that they have their own channels.

As a matter of fact, when a single tube is used in succession for long hours, the degree of the change in the state of stream, such as the amount of flow is non-negligible. For instance, it is not rarely the case that the change in the amount of flow rises over 10% when the tube is in succession for 10 hours. As the thinkable factors of the change in state of stream are pointed out the two become apparent: the change with the passage of time of the tube itself under the pressure of the rollers set on the tube pump, and the other is the contamination due to the adhesion of foreign matters, such as blood-corpuscles, protein, and others contained in the liquid, to the inner wall of the tube. Referring to the former out of the above two factors, since the respective changes with the passage of time of all tubes are different from one another on the basis of the difference in wall-thickness and quality of material and further owing to the subtle unlikeness in construction of the tube pumps used, it may safely be said that it is impossible to predict properly the degrees of their changes. As for the latter factor, on the other hand, it will readily bring about a greater difference between the sample source and the reference liquid source as against the former factor when the separate channel systems are used for each of the both sources because the liquids which flow through the respective channel systems are different in quality.

As a natural consequence, the rate of dilution of the sample and buffer solution, for example, also varies progressively at the time of measurement on the basis of the difference of the way of changing in the state of stream between the channel of the sample source and the channel of the reference liquid source during the continuous measurement, so that the state corrected in accordance with the measured value of the actual dilution ratio at the commencement of the measurement falls gradually into disorder. In the face of such a situation, it is useless even if trying to compensate mutually the respective changes in stream with the passage of the time of both the channel of the same source and the channel of the reference liquid source, because their changes each run independently of other. Further, it is to be noted that it is only on the sensitivity of the sensor that the correction by the reference liquid can be made at any time, while the difference between the changing portion in the channel of the sample source and the changing portion in the channel of the reference liquid source can not be compensated, granting that the mixing ratio of the sample solution to the buffer solution, namely, the dilution ratio is varied, and consequently the measured value obtained in this case comes to include some error.

What is more, although the dilution ratio compensating means using the correcting sample which is regarded as identical with or equal to the above-mentioned sample is effective when the concentration of glucose contained in the sample can be considered unvaried within the time of correction, yet it is difficult in practice to make and use the correcting sample equivalent to the sample under the measurement, because it is a normal thing in fact that the concentration of glucose displays the change with the passage of time during the measurement and yet how it varies can not be foreseen. Suppose the correcting sample is made during the measurement and used, as mentioned above, the making of it not only requires much labor in itself but also the changing portion of the concentration of glucose contained in the sample at the time of correction comes to be exhibited wholly as the error in measurement as it is.

To sum up, there is a possibility of the amount of flow of the time pump changing with the passage of time in every tube of it, so that it is required for reasons of correctness in measurement to compensate these changes one after another. Judging from this point of view, the correcting sample of such a type as in the above-mentioned prior art is said not to be suitable for the purpose of being made one after another during the engagement to be used, and consequently it is impracticable to make the successive compensation by the use of such a kind of a correcting sample.

This invention which has been contrived with the object of eliminating various imperfections in the conventional technique inclusive of the above-mentioned prior art, intends to provide an improved device in which a single channel(tube) is made available in common for both the sample solution and the correcting liquid and on which the blood sugar value can be monitored in succession for long hours with exactitude on the basis of the successive connections of the device itself is conducted. Further, this invention contemplates to provide an improved device on which the sampling can be accurately performed without the dilution ratio showing the scattering caused by the anticoagulant even if catheters would be replaced one by another in the consecutive order as a result of having applied a special shift to the structure of the catheter and also making the catheter have the character of a pump tube.

SUMMARY OF THE INVENTION

This invention has for its object to provide a device for automatically and continuously measuring the constituent parts of the blood without being affected by the fluctuations of the amount of flow due to the contamination and change with the passage of time of the tube forming the measuring channel at the time of measuring automatically and continuously for long hours the concentration of a specified constituent part of the blood which is drawn from a vein of the patient in succession by means of the catheter.

Another object of this invention is to provide a device for monitoring the constituent parts of the blood in succession for long hours with exactitude while making the correction of the device itself by the use of the only one channel being common to both the same liquid and the correcting solution.

A further object of this invention is to provide a catheter in which the pipe is not readily clogged, and which catheter is easily exchangable, and further it is to provide a device on which the accurate sampling can be performed by holding in check the scattering of the dilution ratio of the anticoagulant to the blood at the time of the blood drawing, and by using the catheter also having the character of a pump tube.

BRIEF DESCRIPTION OF THE DRAWINGS

FIG. 2 is a scheme of the state of conveying the liquid in the sampling device;

FIG. 3 gives a series of sketches of the sampling device, in which (a) is a side view and (b) is a top view;

DETAILED DESCRIPTION OF THE INVENTION

The invention will be now described more particularly with reference to the accompanying drawings.

Figure 1:
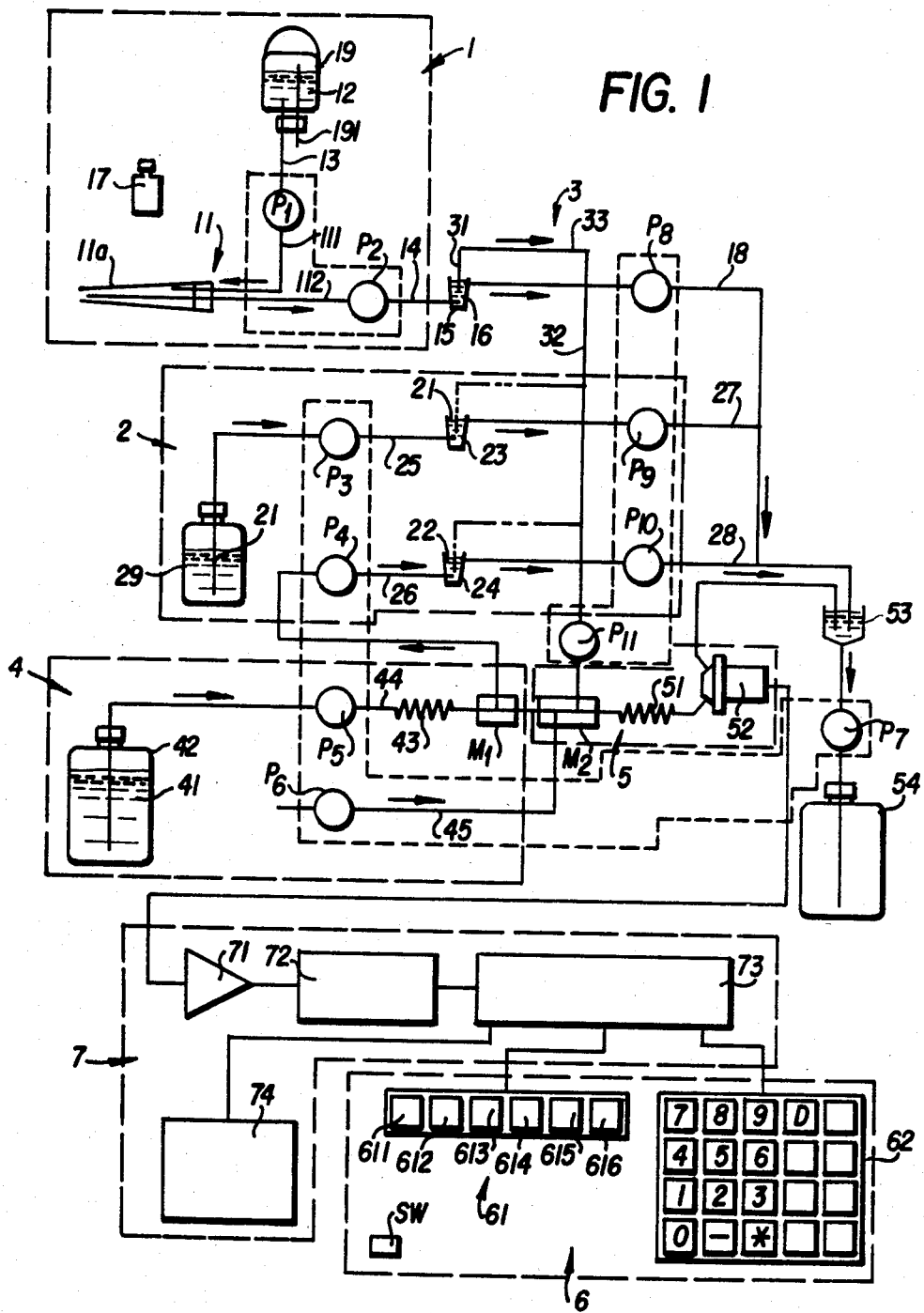
FIG. 1 is a block diagram showing an example of the device according to the invention.

FIG. 1 is a block diagram showing an example of the configuration of a device for automatically and continuously measuring the constituent parts of the blood, according to the invention. This device comprises a blood-drawing section(1), a correction liquid-conveying section(2), a sampling device(3), a buffer solution-conveying section(4), a measuring section(5), an operating section(6), a measuring-controlling circuitry(7), and others.

The blood-drawing section(1) consists of a double-current catheter(11) of a "throwaway" type with a canula(11a), an anticoagulant(12), an anticoagulant-conveying tube pump($P_1$), a blood-drawing tube pump($P_2$), an anticoagulant-conveying tube(13), and a blood-drawing tube(14). In this connection, the reference numerals(111) and (112) indicate a first catheter tubing for introducing the anticoagulant(12) into the canula(11a) and a second catheter tubing for withdrawing a mixed liquid of the blood with the anticoagulant out of the canula, respectively. The blood from the subject (not shown) is diluted by the anticoagulant(12) at the front end part of the catheter(11) which has been inserted into the canula(11a), is drawn in succession while being treated with anticoagulant, and is conveyed from there to a sample liquid cup(15) in which a determinate quantity of sample liquid is to be accumulated. Incidentally, the anticoagulant used here is made by dissolving heparin or the like in physiological saltwater. In the sample liquid cup(15), when the liquid measure goes beyond the limit of the determinate quantity, the extra quantity overflows and is drained. Like this, the sample liquid cup(15) is designed so as to adopt to the working of keeping always a determinate quantity of fresh sample liquid(16).

The tube pumps($P_1$) and ($P_2$) are driven coaxially, but as previously mentioned, it is very difficult to select the characteristics of the tubes(13) (14) and the tube pumps ($P_1$).($P_2$) so that they behave identically. Accordingly, the accurate ratio of the quantity of the anticoagulant convyed by the pump($P_1$) to the quantity of the blood drawn by the pump($P_2$), in other words, the dilution ratio between them must be determined by the use of the standard liquid II(17) of a known concentration. How to determine the dilution is described later. As for obtaining a definite value of the dilution ratio independently of the geometry of both tubes(13) (14) in the blood-drawing section, it would be expected to some extent by heightening the concentration of the anticoagulant(12) and therewith reducing the quantity of it which is to be added, thereby bringing the dilution ratio close to 1 (the numeral value of one). Further, in the present example, a double-current catheter of the "throwaway" type is used in order to dilute the blood with the anticoagulant, however, it does not matter if a single tube-type catheter is employed instead. In the latter case, the question of the dilution ratio in the blood-drawing section can be also solved by coating the inner wall of the single tube with anticoagulants (heparin, for example) or fibrinolysozyme (mainly, urokinase).

In the correction liquid-conveying section(2), the standard liquid I(21) and the base liquid(22), both being necessary for the successive correction, are conveyed continuously to the standard liquid cup(23) and the base liquid cup(24), respectively, by the aid of the tube pumps($P_3$), ($P_4$). The standard liquid cup(23) and the base liquid cup(24) are always filled with the respective fresh liquids in their own determinate quantities, when their extra liquids each overflow and are drained, as described after. In this connection, because the present example makes use of the buffer solution(41), described later, as the base liquid(22), it is arranged to be conveyed from the buffer solution container(41), but it is good of course if it is also conveyed from a base liquid container provided separately. On the other hand, the standard liquid I(21) is conveyed from the standard liquid I container(29). The reference numerals(25) and (26) in the figure indicate the tube for conveying the standard liquid I and the tube for conveying the base liquid, respectively.

The sampling device(3) is designed in such a manner that the sampling nozzle(31) sucks up the liquids from the sample liquid cup(15), the standard liquid cup(23), and the base liquid cup(24) in predetermined sequence in the measuring-controlling circuitry(7) with the help of the tube pump($P_{11}$), and that the liquids such sucked is conveyed through the nozzle tube(32) to the manifold of the measurig section(5). The details of the working will be described later. Incidentally, it is desirable in this case to provide a washing tub apart from the above, when the nozzle(31) is set so as to be immersed also in this washing tube in prescribed order.

In the buffer solution-conveying section(4), the buffer solution(41) is divided into two parts by the manifold ($M_1$) after having been made homothermal by letting pass through a heat exchanger(43) in advance, out of which two parts one is conveyed in succession to the base liquid cup(24), and the other to the manifold($M_2$) for use in being mixed with the sample liquid, the standard liquid 1, and the base liquid, separately. The reference symbols($P_5$) and ($P_6$) in the figure indicate a tube pump sending the buffer solution(41) through the tube(44) to the heat exchanger(43), and another tube pump feeding air through the tube(45) into the manifold($M_2$), respectively. These tube pumps($P_5$), ($P_6$) are driven coaxially in the same way as the before-mentioned tube pumps($P_3$), ($P_4$) in the correction liquid-conveying sections(2) and the tube pump for draining($P_7$) described later.

In the measuring section(5), as mentioned above, manifold($M_2$) is provided, to which the buffer solution(41) made homothermal is conveyed through the manifold($M_1$) of the buffer solution-conveying section(4), and also air for branching the stream of the buffer solution(41) is sent. Into this branched buffer solution is poured the sample liquid(16), the standard liquid I, and the base liquid, and then they continue to flow away all together as a measuring liquid. The branching of air is for the object of preventing the diversion of the measuring liquid and obtaining the mixing effect of it, and thereby the washing effect of the wall is also expected. The measuring liquid is commingled upside down while passing through the mixing coil(51), and then it is sent to the fixing enzymic membrane electrode(52) which is made up of, for example, the combination of the glucose oxidase fixing membrane and the hydrogen peroxide electrode and which is for use in measuring the concentration of glucose, whereat the concentration of glucose is measured. In this case, the air layers and the measuring liquid layers run on the electrode(52) alternately one behind another without air bubbles being defoamed. The measurement continues to be done while all the measurement system inclusive of the electrode(52) being washed by the action of the airbranching, so that the mutual contamination among the measuring liquids can be reduced to a minimum. The liquids and bubbles which have finished the measuring work pass through the drain cup(53) and are exausted into the drain bottle(54) by the action of the tube pump for draining($P_7$) lying between the cup(53) and the bottle(54). Also all liquids which have overflowed the before-mentioned cups(15), (23) and (24) are conveyed into the same drain cup(53) through the respective courses of the tube for sample liquid overflow use(18) and the tube pump($P_8$) for the same use as above, the tube for standard liquid I overflow use(27) and the tube pump($P_9$) for the same use as above, and the tube for base liquid overflow use (28) and the tube pump($P_{10}$) for the same use as above, and they drain therefrom into the drain bottle(54) all together. The above tube pumps($P_8$), ($P_9$), ($P_{10}$) and the tube pump for sampling use($P_{11}$) are driven coaxially. However, the before-mentioned tube pumps $P_1 \sim P_2$, $P_3 \sim P_7$, and $P_8 \sim P_{11}$ need not be driven by the coaxial driving of multiple head-type, but by may be driven respective single drives separately.

In the operating section(6) which takes charge of the operation of the apparatus in it entirety, the actual use of the machine is put into execution of the manipulation of the operating switch plate(61) and the key board(62). Keyboard (62) is a conventional keyboard used to enter data into microcomputer (73).

Lastly, the measuring-controlling circuitry(7) comprises an I-V converter(71), and A-D converter(72), a microcomputer(73), and an indicator(74), wherein the values of the blood sugar are displayed on the indicator(74) in due order after the output signals from the glucose electrode(52) have been treated and corrected successively, and at the same time the behavior of the sampling device(3) is controlled. Microcomputer (73) is connected to tube pumps ($P_8$), ($P_9$), ($P_{10}$) and ($P_{11}$) and to motor (337) to control their operation.

Microcomputer (73) is also coupled to sensor (52) to receive appropriate input information.

Microcomputer (73) may be any conventional microcomputer which can provide output signals and receive input signals and which can be programmed to provide and receive the output signals and input signals.

The programming is also conventional in nature and used to control the operational process of the invention as described below.

The invention will be now described in order of the operational process.

After the arrangements of all sorts of correcting liquids and others have been done in due form, the power switch(SW) in the operating section(6) is turned on to actuate all of the tube pumps($P_1$)$\sim$($P_{11}$) and to input the datings and numbers into the microcomputer(73) by the use of the key board (62). When the prescribed warm-up has been completed, the stand-by lamp(612) in the operating switch plate(61) lights, while the pump lamp(611) goes out and all the pumps come to a stop. Then, when pushing the calibration switch(613), the pumps start operating again, and also the sampling device(3) goes into action. Now, the catheter(11) is inserted together with the canula(11a) into the standard liquid II(17), and the time lag having elapsed between from the suction of the mixed solution of the liquid(17) and the anticoagulant(12) until its inflow into the sample liquid cup(15) is measured by the use of a stop watch or the like. This measured time is input through the key board(62) in order to be used for the subsequent measurements. The time lag here can be regarded as substantially constant so far as the specification of the catheter does not vary. Accordingly, if once having been determined, it is good enough at the time of replacing the catheter together with the canula later on if only this measured value of the time lag is input. Subsequently, the dilution ratio of the blood to the anticoagulant of the blood-drawing section(1) determined by the use of the standard liquid II(17) as a substitute for the blood is made stored in the microcomputer(73) to be used for the subsequent measurements. The measurement of the dilution ratio at the blood-drawing section(1), however, may be omitted, for example, by using the catheter of a single tube-type which is coated on its inner wall with the anticoagulant.

When the catheter(11) has been inserted in the patient, the blood is diluted at the above-mentioned dilution ratio while being treated anticoagulatingly, and is conveyed continuously into the sample liquid cup(15). The cup(15) is made in such a construction that when the liquid measure of the sample liquid(16) goes beyond the limit of a determinate quantity, the extra liquid overflows of itself and is discharged into the drain bottle(54), whereby a determinate quantity of fresh sample liquid(16) is always kept in the cup(15). Therefore, although the nozzle(31) sucks respectively the sample liquid (16), the standard liquid I(21), and the base liquid(22) in order, the occurrence of the mutual contamination of them can be avoided.

The sample liquid cup(15) is usually replaced for every patient, but it may be reused if it is rinsed, otherwise it is also preferable to use a "throwaway-type". When using the "throwaway-type", the cup(15) may be made in combination with the blood-drawing tube(14) of the double-current catheter(11) integrally.

When pushing the check switch(614) this time, the values of the blood sugar starts being measured continuously.

Firstly, the sampling nozzle(31) sucks a determinate quantity of the standard liquid I(21) from the standard liquid cup(23) on the prescribed system. By way of example, it sucks the liquid(21) in the state of being divided by the air branching into two parts, as shown in FIG. 2, for 20 seconds. The the nozzle(31) moves into the base liquid cup(24) and sucks the base liquid(22) into the prescribed state, to take an illustration, in the state of being divided by the air branching into 8 parts, as shown in FIG. 2, for 40 seconds. Subsequently, the nozzle(31) goes into the sample liquid cup(15), and sucks the sample liquid(16) on the prescribed system, that is, in the state of being divided by the air branching into 2 parts, as shown in FIG. 2, for 20 seconds, in the same manner as the case of the standard liquid I(21). At this time, it is important to equalize substantially the way of sampling both the sample liquid(16) and the standard liquid I(21) as to the quantity of sample, how to divide segments, etc. This is for providing against the possibility of the quantity of sample, etc. influencing responses in the region of the electrodes, when these liquids(16), (21) are diluted equivalently by the buffer solution, as discussed below. The nozzle(31) goes further into the base liquid cup (24) to suck the base liquid(22) for 40 seconds in the same behavior as described before. After that, the nozzle(31) moves again into the standard liquid cup(23) and repeats the foregoing motion. In FIG. 2, the abbreviation AIR stands for the air branchings, and the STD, the BASE, and the SAM are short for their respective bubbles of the standard liquid I(21), the base liquid(22), and the sample liquid(16) which each are divided by the above air branchings. It is possible to prepare the air branchings in suitable sizes, at any intervals, and in optional numbers.

The shifting of the nozzle(31) is conducted by the nozzle-holding arm driving mechanism which is, for example, as shown in FIGS. 3(a) and (b). The nozzle(31) is first inserted fixedly into the vertical through-hole(331) at the front end part(33a) of the nozzle-holding arm(33). Onto the top part of the nozzle(31) is fitted a nozzle tube(32) which is connected to the tube pump($P_{11}$) for sampling use. As for the nozzle arm(33), it is supported both by a fulcrum rod(333) which transversely passes through a slot(332) bored on the side of the rear half part(33b) of the nozzle-holding arm(33), and by a disk(335) buttressing up a pin(334) which is provided protrusively on the side of the middle part of the nozzle-holding arm(33). The pin(334) is floatingly put into a through-hole(336) on the peripheral region(in the figure: at the left side) of the disk(335). In proportion as the disk(335) is rotated by a motor(337) through a disk crank(337') and a rod(338) at a certain angle, for example, at an angle of 180 degrees in the direction of the dotted line arrows, the pin(334) rotates in the direction of the full line arrows, thereby causing the front end part (33a) of the nozzle-holding arm(33) to move back and forth while tracing a circular arc, as shown in FIG. 3(a). In this connection, the reference numeral(339) in the figure indicates the center shaft which is positioned fixedly, and the numeral (340') indicates a pin which interconnects the disk(335) and the rod(338). As a necessary consequence of the above-mentioned rotation of the disk(335), the nozzle(31) together with the nozzle-holding arm(33) reciprocates between the full line position and the broken line position. When being in the full line position, the nozzle(31) is inserted into the base liquid cup(24), whereas when coming in the broken line situation, it is put into the standard liquid cup(23) and the sample liquid cup(15) in order. The standard liquid cup (23) and the sample liquid cup(15) both are mounted on a slide base(34) which moves back and forth by the action of an eccentric cam(341) being rotated by a motor(343) in combination with a spring(342) otherwise a rack and pinion (not shown) to bring both the cups(23), (15) successively to their own sucking positions. The motion of the arm(33) and the slide base(34) is controlled by a microcomputer(73). Referring to the way of driving the nozzle-holding arm(33), there is also conceivable besides the above-mentioned such a one as of a system on which the disk(335) is rotated by some electrical or mechanical means, for example, the combination of a photomicrosensor and a stopping motor, etc.

In the present example, it requires two minutes to one measuring cycle, as seen in FIG. 2. That is, it may be said that, in this invention, the measurement of the sample liquid is not all continuously done in the strict sense of the word. However, since the value of the blood sugar in the sample liquid tends to vary rather smoothly, as an example is given in FIG. 4, and therefore it is not threatened with the abrupt change at least at intervals of so much time, the measurements done at intervals of two minutes are significant enough to be compared favorably with the continuous measurements. Nevertheless, this does not mean that the characteristic of our invention lies in the point that the cycle of the measurement repeats at intervals of two minutes, but it goes without saying that it does not matter if the cycle is set at intervals of shorter or longer times than the above two minutes.

The standard liquid(21), the base liquid(22), and the sample liquid(16), which are all obtained, for example, in such a manner as shown in FIG. 2, each pass through one and the same channel, namely, the nozzle tube(32) to be conveyed into the manifold($M_2$), where each of them is diluted in the same way and at an equal ratio by the buffer solution(41) which has been made homothermal, is separated through the interposition of several air layers, and is sent to the mixing coil(51) as the respective measuring liquids for standard liquid use, for base liquid use, and for sample liquid use in due order. These measuring liquids each are stirred to being homogeneous, and then flow successively into the glucose electrode(52) in the state of being separated by the air layers, wherein each of these measuring liquids comes to be measured.

At this time, the signals from the electrode(52) pass through the I-V converter(71) and the A-D converter(72) successively, and then enter the microcomputer(73). These signals each represent the measured value of the standard liquid I(21), that is, the standard value, the measured value of the base liquid(22), that is, the base value, and the measured value of the sample liquid(16), that is, the test value. It is to be noted that these three measured values are such ones that have been obtained on the basis of the measurement of each of the liquids(21), (22) and (16) which were diluted in the same way in the course of flowing through one and the same channel in all the measuring channels of the nozzle(31) and downward. It is usual that there occur some changes in the state of flowing with the passage of time in the channels using tube pumps, as stated previously, however, in the case in question because the channel to these three liquids(21), (22) and (16) is entirely one and the same, the changes in the state of flowing through the channel, namely, the nozzle tube(32) offset one another, and therefore their mutual influence is able to be compensated. Contrary to this, in the case of letting the sample liquid and the correcting liquid flow through the separate channels, it becomes impossible to compensate the changes in the state of flowing, as mentioned above.

Figure 5:
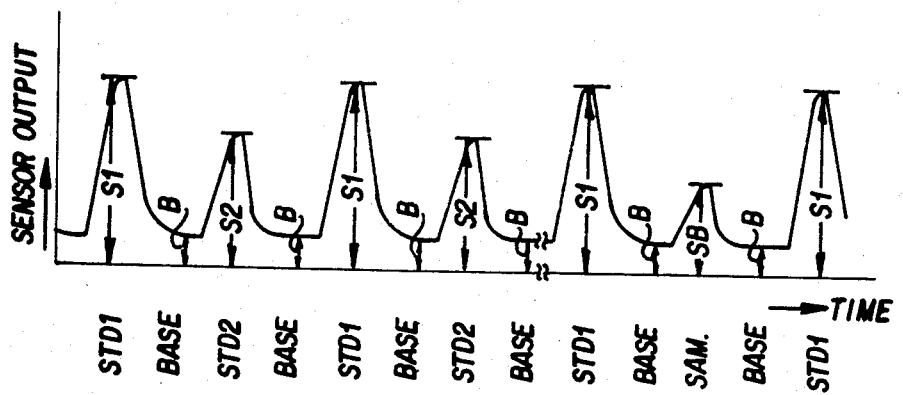
FIG. 5 is a graph showing the temporal changes of the electrode output.

Description will be now directed with the aid of FIG. 5 to the system on which the value of the blood sugar is calculated by means of the signals from the electrode(52).

In the figure, the axis of abscissas denotes the time, and the axis of ordinates denotes the output (to be more precise: the average count number of the shifting output) from the electrode(52). $S_1$ in FIG. 5 represents the maximum values at each time of having measured the standard liquid I, SB the maximum values at each time of having measured the sample liquid, and B the minimum values at each time of having measured the base liquid directly after the standard liquid I. If the dilution ratio D is explained being based on FIG. 5, it is represented by the following equation:

$$D = \frac{S_2 - B}{S_1 - B} \times \frac{C_1}{C_2}$$

where $S_2$ denotes the maximum value at the time of having measured the mixed solution of the standard liquid II(17) with the anticoagulant (12), and $C_1$ and $C_2$ denote the concentration of the standard liquid I and the concentration of the standard liquid II, respectively, both being of known the value of the blood sugar in the sample liquid: B.G. The value of blood sugar of the sample liquid is expressed using the values of $S_1$ and B directly prior to it and it is determined on the basis of its net test value: SB-B accounting for how many percent of the net standard value just before it: $S_1 - B$, namely, $$B.G = \frac{1}{D} \times \frac{SB - B}{S_1 - B} \times C_1$$

In this connection, it may be also good if the values of $S_1$ and B for use in measuring are found by the different way of finding, for example, calculating by the use of the values: B directly before and $S_1$ directly after the test value in FIG. 5. In this case, however, there is the necessity of successively correcting the span of measurement, that is, $S_1 - B$ because that the state of flowing usually changes with the passage of time when using tube pumps, so that it is obviously advantageous to use the values of $S_1$ and B which are obtained from the spot close to SB as the signal of the measured object.

As seen from the above, the measured values are corrected in succession in our invention, so that they are not susceptible to influences of the changes in the state of flowing through the channel, and what is better, this successive correction exhibits a prominent effectiveness for the reason that the standard liquid I and the base liquid are used as two different correcting liquids, and further that these correcting liquid and the test liquid flow together through one and the same channel.

Figure 6:
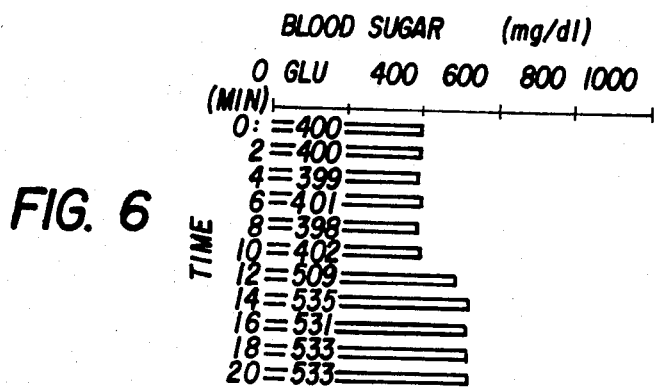
FIG. 6 is another measurement example which represents graphically the measured results of the value of blood sugar in the START mode.

In this way, the value of the blood sugar contained in the sample liquid is measured in succession, for example, every two minutes and is displayed on the indicator (74), for example, in a bar graph-form as illustrated in FIG. 6, whereat the axis of ordinate give the time, and the axis of abscissa expresses the quantity of the blood sugar BLOOD GLUCOSE (mg/dl).

Figure 4:
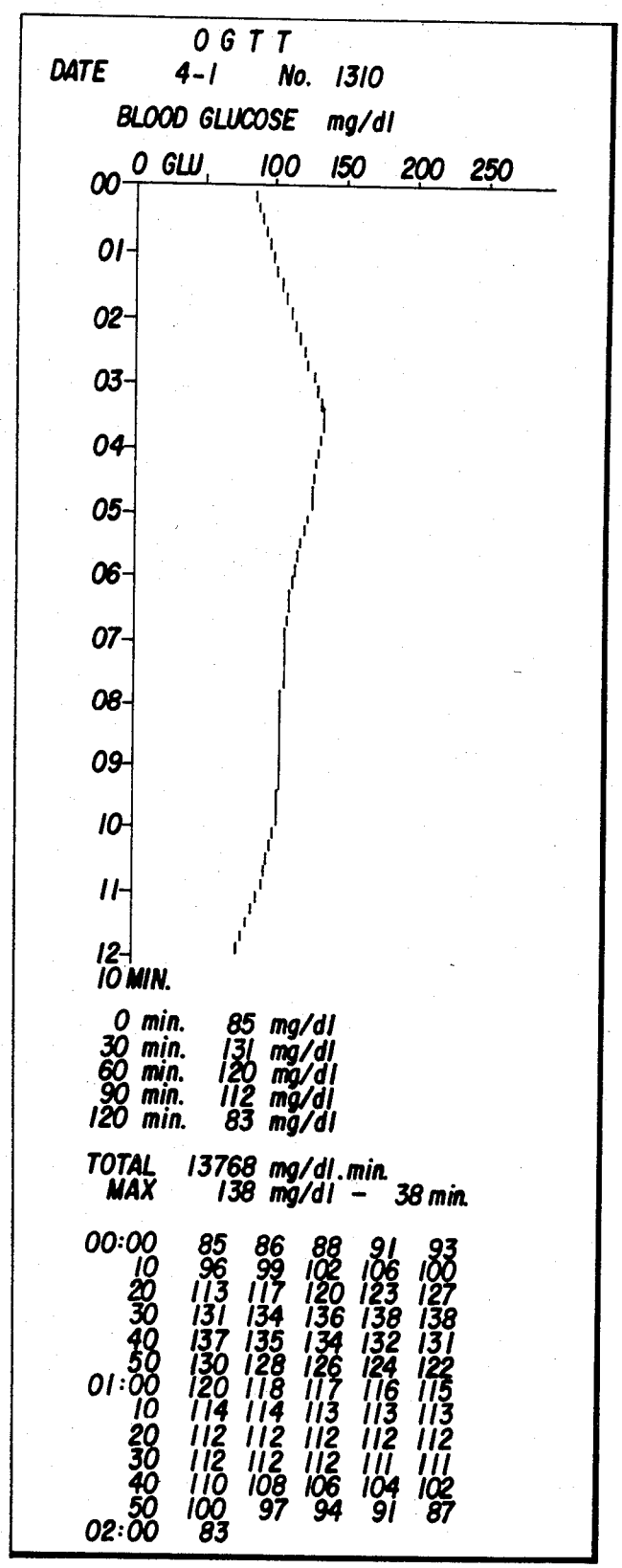
FIG. 4 is a graphic chart showing the measured results in the Personal Sugar Load Test (OGTT) mode.
Figure 7:
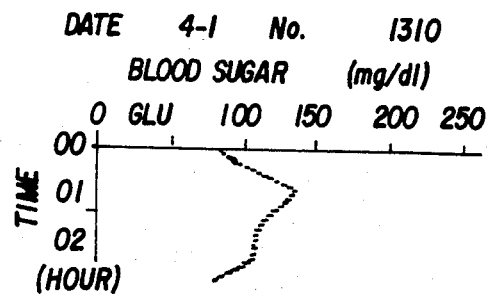
FIG. 7 is a graphic chart showing a modified example of FIG. 4.

On the other hand, the operating switch plate (61) is also provided with the starting switch (615), and thereby is adapted to the use for various kinds of loading tests. In measuring OGTT (Personal sugar load test), for example, if the duration is calculated from the time when the start switch (615) is set ON at the starting time of the sugar load per as, the measurement proceeds just as the case of the foregoing check switch (614), and thereby the measured value can be obtained with the lapse of time. Further, when the display of the results of the measurement in relation to OGTT mode is indicated by the use of the key board (62), there are displayed after the completion of the measurement for two hours the value of the blood sugar at every two minutes, the total quantity of the blood sugar during two hours, and the maximum value of the concentration along with its appearance time at some point of time within two hours; to say nothing of the values of the blood sugar to the actual time, such as the value of the blood sugar at the end of 30 minutes after the sugar loading, the value of the blood sugar after 60 minutes, the value of the blood sugar after 90 minutes, and the value of the blood sugar after 120 minutes. FIG. 4 gives an example of the results of the measurements like the above-mentioned (the subject here is different from the one in FIG. 6). FIG. 7 is the one that rearranges the graph of FIG. 4 by shortening the axis of time. This makes the peaks more intelligible as against FIG. 4. It may be good that the graph of FIG. 7 is used in place of or in combination with the graph of FIG. 4.

The liquids and bubbles which have been through with the measurement at the electrode (52) are exhausted through the drain cup (53) into the drain bottle (54). It has been already described that all of the liquids having overflowed each of the cups (15), (23) and (24) are also drained into the drain bottle (54).

When a series of measurements comes to an end, the operation of the apparatus stops by pushing the stop switch (616).

With the above, the description of the measuring system from the sampling nozzle downward as the basis of the present invention is over. Description will be now directed to the catheter constituting the blood-drawing section (1).

For the catheter, there is often used a single tube-type which is coated at its inner wall with some anticoagulant. However, it is usual that the double-current catheter is being used which drawn the blood at the same time while infusing the anticoagulant. In the case of using such a double-current catheter, this invention describes a new design so as to be able to obtain the accurate dilution ratio exclusively by the use of the standard liquid II (17).

Figure 8:
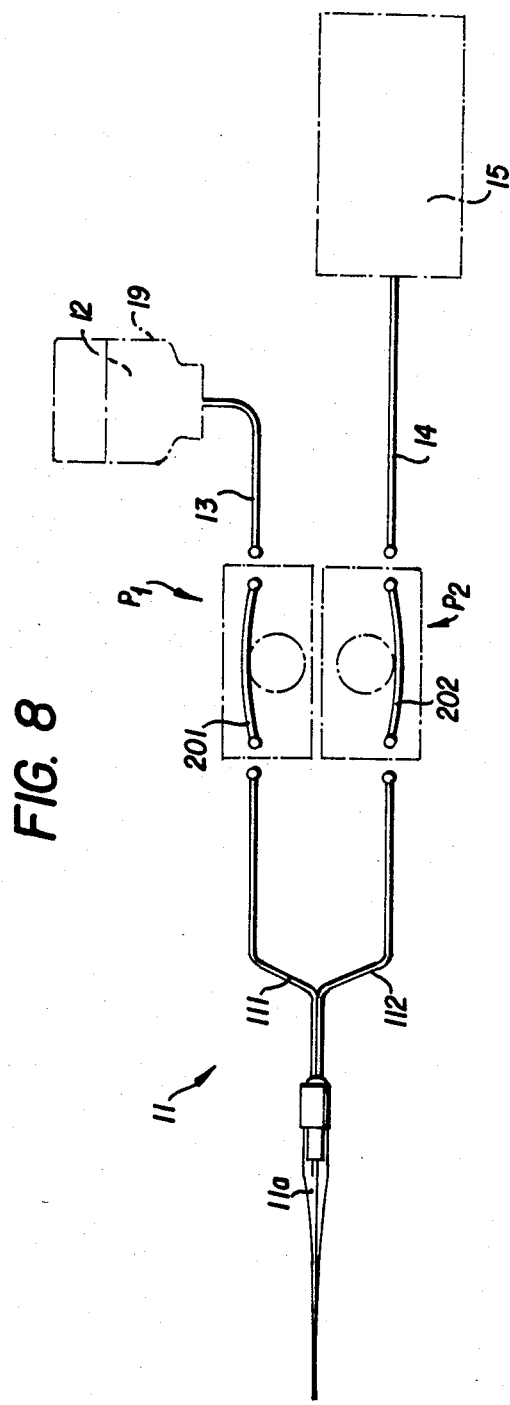
FIG. 8 is a schematic diagram showing an example of the blood-drawing part of a type using a conventional double current catheter.

Heretofore, the double-current catheter (11) of this kind is put in practical use in such a state as shown in FIG. 8. The first and second catheter arrangements (111), (112) of this catheter (11) each are connected to the respective pump tubes (201), (202) of the tube pumps ($P_1$), ($P_2$) (In the figure, the separate pumps are used, but it does not matter of course if a single pump of a multihead-type is employed), where the front portions from the catheter arrangements (111), (112) forward are designed in the form of a throwaway-type so as to be replaceable at every patient. Incidentally, there is preferrably used such a kind of pump tube of about 0.2 ~ 1.0 m/m in inner diameter as made of silicone or Tigon (trademark of the Norton, USA). Further, the anticoagulant-conveying tube (13) and the blood-drawing tube (14) each are also connected to the respective pump tubes (201), (202). This is according to the reason that the pump tube itself is necessary to be exchanged in about several decades to a hundred hours.

For all that, the above-mentioned conventional system has various defects as follows.

In the first place, since the quantity of discharge (or the quantity of suction) of the above tube pumps depends on the inner diameter of the pump tubes (201), (202) and is proportional to their cross-sectional area, the quantity of discharge varies in proportion to the size variations of the inner diameter. In these circumstances, every kind of exertion is being used in order to make the diameter of all pump tubes uniform. However, it is very hard to finish the tolerance of the inner diameter up to the precision better than 0.5±0.05 m/m, for example, in the case of the silicone tube of 0.5 m/m inner diameter even though having molded the tube scrupulously. Then, in practice, it is the actual facts that a certain number of tubes selected from the carefully molded ones are subjected further to the size inspection, out of which the tubes being within the limits of desired tolerance are sorted out and put in use. In this connection, in the case of the selective use of the tube regarding the tolerance of the inner diameter as being 0.5±0.05 m/m, the fluctuation of the quantity of discharge at the time when the pump tube is exchanged amounts to about one and a half (1.5) times according as the cross-sectional area increases from $0.45^2$ to $0.55^2$. This is a considerable quantity of change.

This change in the quantity of discharge causes the mixing ratio of the anticoagulant to the blood to be changed in the case of the double-current catheter using two pump tubes. Especially, in order to reduce the quantity of blood-drawing and to shorten the time lag attributable to the catheter arrangements, it is possible to think of a method for introducing the anticoagulant and the blood into the measuring device while increasing the quantity of flow of the former and diluting the latter at the high dilution ratio. However, in order to set the quantity of infusion of the anticoagulant and the quantity of suction of the blood from the inner vein at an approximate value, the above-mentioned change in the quantity of discharge makes very difficult the attainment of the desired stable mixing ratio. Not only that, there are many cases where it is impossible to let them act with a substantially approximate quantity of flow, and it becomes difficult to perform the samping of the blood at a high dilution ratio.

Secondly, about the catheter arrangements (111).(112) as well, there happens the problem of the size tolerance as mentioned below:

For the cathether arrangement, there is perferrably used as a suitable material the silicone tube of 0.2 to 0.8 m/m in inner diameter which is flexible, not hemolytic, and physiologically inactive. However, if the inner diameter of the catheter arrangements differ at each time of exchanging the catheters, it follows that the time lag varies in the first and last catheter arrangements, admitting that the quantity of suction of the pumping means remains constant. This arouses an important problem concerning the performance of the apparatus in the measurement taking into consideration the time factor, for example, the sugar load test for estimating the metabolic rate of the subject. Of course, as a counter-measure to avoid this problem, there is a means for correcting the time lag of such a sort with the aid of calculating the time required for those liquids to flow from the pointed end of the canula (11) into the sample liquid cup (15) at each time of exchanging the catheter arrangements or the tube pumps by the use of a stop watch or the like. Such a means, however, is too intricate and hard to operate.

Thirdly, the catheter arrangements and the pump tubes are very small in inner diameter, as mentioned above, so that there is a fear of foreign matters being liable to deposit at such spots as the connections which have difference in level, and also the tubes becoming clogged. Further, blood corpuscles, blood plasma and protein may so that it is preferable to exchange such arrangements and tubes at every time of the measurement. The exchanging job, however, is troublesom in the presence of a considerable number of the connected spots.

Any of these defects results from the construction made in such manner as to try to connect one another the pump tubes (201), (202), the catheter arrangements (111).(112), and the tubes (13), (14) which all have been formed separately.

In view of these circumstances, the present invention contemplates to eliminate the above-mentioned defects by prolonging each of the catheter arrangements (111),(112), by connecting each arrangement with each of the pump tubes (201),(202), the anticoagulant-conveying tube (13), and the blood-drawing tube (14) integrally, and by incorporating each of the catheter arrangements directly into the respective tube pumps, and in this way it provides a device for automatically and continuously measuring the constituent parts of the blood which is easy to use with more exactness in combination with the above-mentioned measuring system.

Description will be now directed to the preferred example of both the improved double-current catheter having the catheter arrangements and the tube pumps used in the blood-drawing section (1) with reference to their respective drawings.

Figure 9:
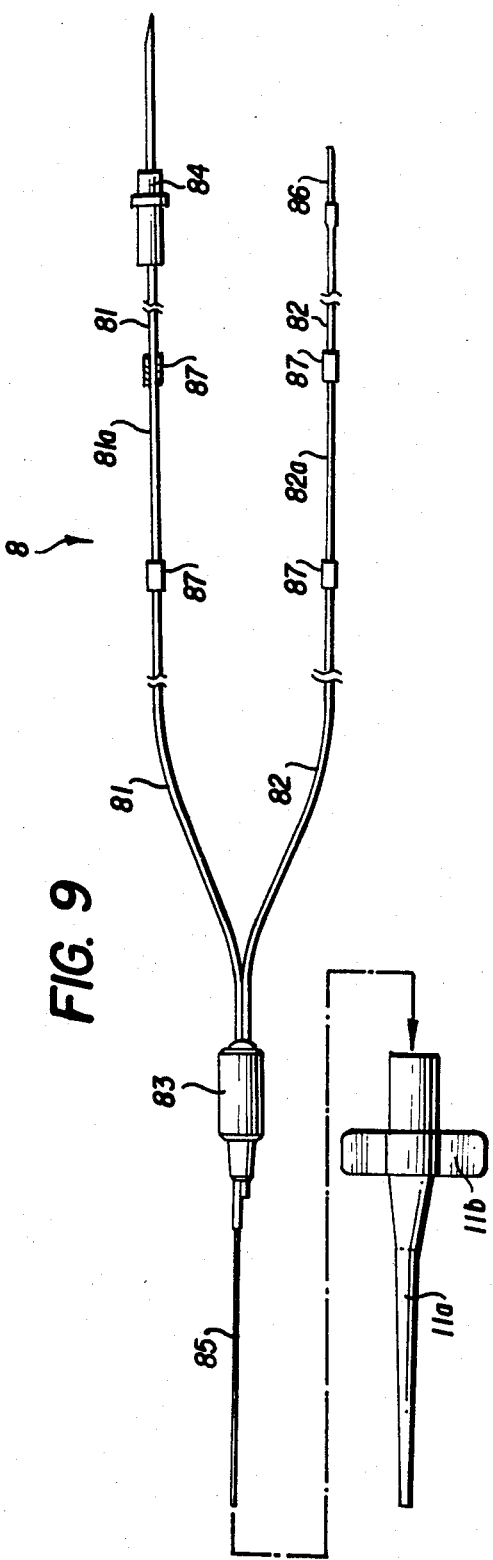
FIG. 9 is a top view of an improved double current catheter according to the invention.

FIG. 9 shows an example of the improved double-current catheter (8).

A first catheter arrangement (81) and a second catheter arrangement (82) both are conveyed at their front end part by a nipple (83) so as to be insertable into the canula (11a). The tip of the first catheter arrangement (81) (used for infusing the anticoagulant) protrudes a little from the nipple (83) so as to be able to fill up the interior of the canula with the anticoagulant, whereas this arrangement (81) is provided at its rear end with a bottle needle (84) which is to be inserted into an anticoagulant container (19). The second catheter arrangement (82) (used for taking-out the mixed liquid) is connected at its tip to a small tube (85) which sucks the mixed liquid (sample liquid (16)) at the front end part of the canula, and is provided with a connecting pipe (86) which couples onto a sample liquid cup (15). These two catheter arrangements (81),(82) are made of silicone tubes which are about 0.2~0.8 m/m in inner diameter and about 0.6~2.5 m/m in outer diameter. For the above-mentioned small tube (85) is preferably used the one which is smaller than the above two and is made of Teflon (trademark of the Du-Pont).

For the canula (11a) is also preferably used the one made of Teflon and the like which possesses the flexibility and is excellent in antithermbosis, bu the one shown in the figure is equipped at its basal part with a wing (11b), which wing is fixed on the punctured region of the patients' body with some adhesive tape or the like in order to prevent the canula (11a) attached to the patient from its shifting or falling-off.

Further, the two catheter arrangements (81),(82) each are provided with two by two stoppers (87) at their respective middle parts leaving definite intervals. These intervals constitute the respective fitting parts (81a),(82a) of the tube pumps. These two tube pump-fitting parts (81a).(82a) correspond to the pump tubes (201),(202) according to the conventional system (FIG. 8) and the bottle needle (86) side from the fitting part (81a), and the connecting pipe (86) from the fitting part (82a) correspond to the conventional anticoagulant-conveying tube (13) and the blood-drawing tube (14), respectively. Incidentally, in the one which incorporates a trap (not shown) within the anticoagulant-conveying channel, the rear end part of the first catheter arrangement (81) may be used whether it is connected to this trap or it is formed integrally with that.

Figure 10:
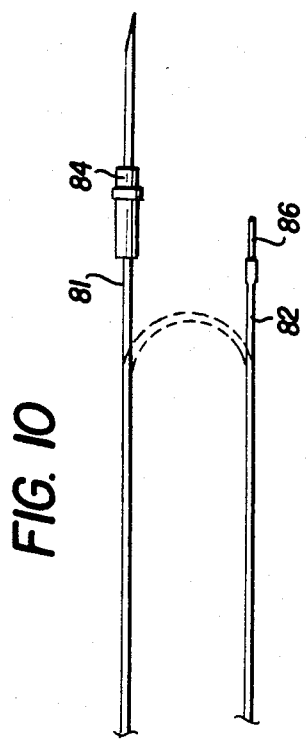
FIG. 10 is an explanatory diagram showing part of the procedure of making the catheter arrangement of the improved double-current catheter.

In the second place, FIG. 10 is an explanatory diagram as to how to make the improved double-current catheter (8). As seen in the figure, a single tube being continuous in a string is cut at its middle part in two halves. To the cut parts are attached the bottle needle (84) and the connecting pipe (86) separately. Thus, each of these half tubes are made so as to constitute the first catheter arrangement (81) and the second catheter arrangement (82). This is on the ground that as a result of these tubes at issue being usually extrusion-molded silicone tubes, even the tubes worked at the same time are likely to have a fluctuation in size owing to the stability of the extruding machine and the vulcanization conditions. Therefore, uniform size is hard to procure, and in addition they give rise to the size distribution undulating in the longitudinal direction. However, the fluctuation in size to such a degree is negligible because they are worked by the almost indentical molding condition at the two neighboring spots.

Figure 11:
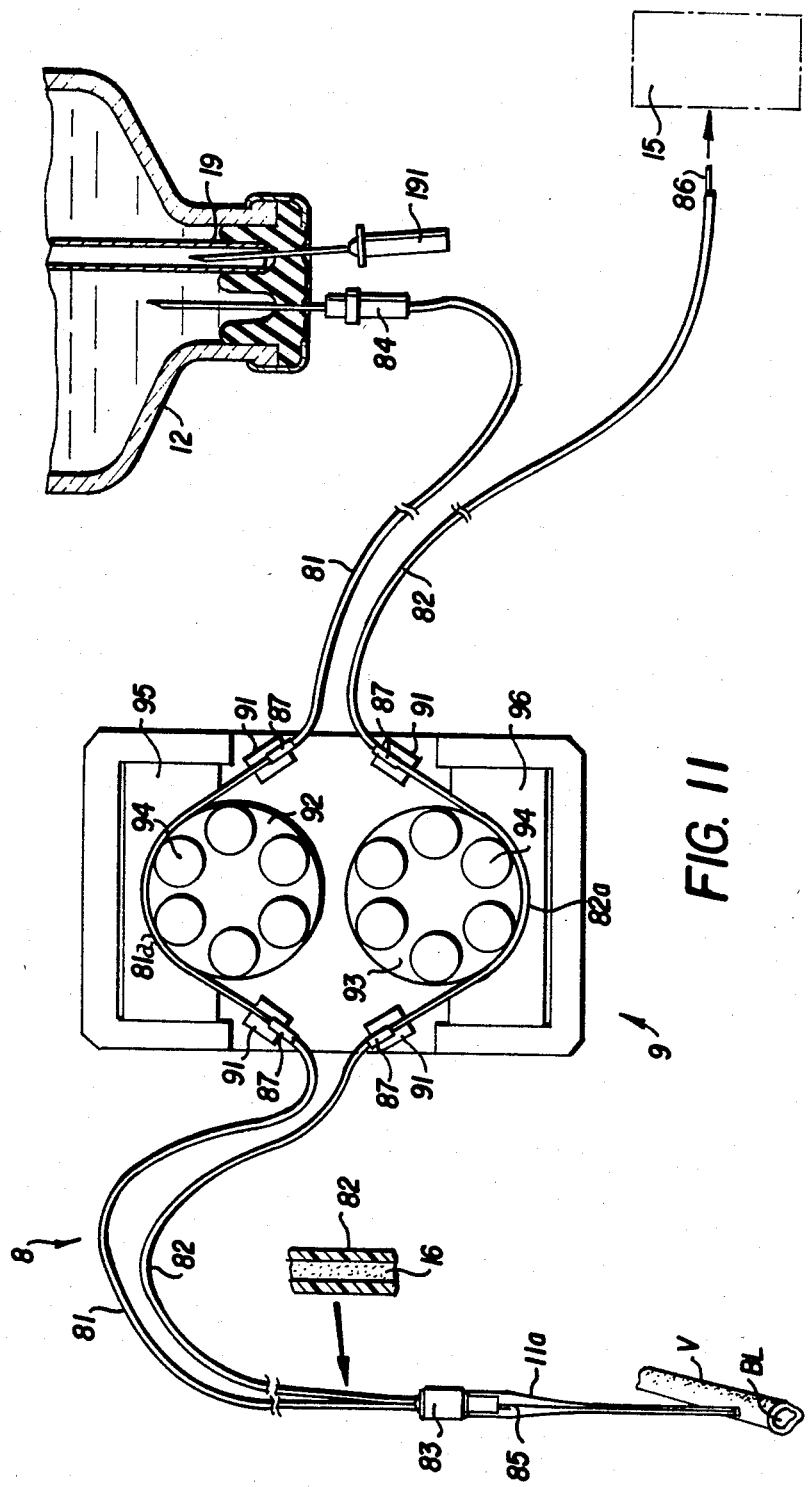
FIG. 11 is a plan view showing an example of the blood-drawing section according to the invention.

The double-current catheter (8) according to the invention as described in the above, has several features worthy of attention as described hereinbelow;

Firstly, because the two catheter arrangements (81),(82) are constructed by the use of the respective tubes being continuous in a string, the difference in inner diameter between the tube pump-fitting parts (81a),(82a) forming the segments of the arrangements and the other parts is negligible and further the difference in level does not lie between them. Secondly, the tube pump-fitting parts (81a),(82a) of the respective catheter arrangements are close to the place where a single tube has been cut in two, and accordingly the difference in inner diameter between them is also negligible. Such features exhibit the excellent effects and come to solve all of the controversial points immanent in the above-mentioned conventional double-current catheter (11). In what manner does the effect and working of these features progress will be now described in the following with reference to FIG. 11.

Figure 12A:
FIG. 12(a) is a sectional view of the part of the catheter arrangement being provided with a stopper.
Figure 12B:
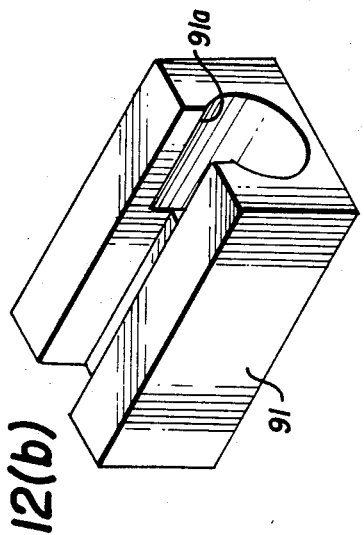
FIG. 12(b) is a perspective view showing an example of the tube guide.

A tube pump (9) which is suitable for both the infusion of the anticoagulant (12) and the suction of the sample liquid (16) is of the multiroller-type having 2-channel discharge heads known in the art. The fitting of the catheter arrangements (81).(82) in the tube pump (9) is done by setting the tube pump-fitting parts (81a),(82a) at the drawing positions of the head parts while hanging the stoppers (87) provided two by two on the tube guide (91). The stopper (87) is covered and adhered with another tube which has an inner diameter a little larger than an outer diameter of each of the catheter arrangements (81),(82), as shown in FIG. 12(a). The tube guide (91) is of such a construction as shown in FIG. 12(b), while the stopper (87) is set being caught in the stopper receiver (91a). However, it will do well if these stopper (87) and tube guide (91) only have such a form as being able to attach the catheter arrangements to and detach them from the tube pump (9) simply and certainly, so that they are not always limited to the above-mentioned example. Of course, it will be all right if there is adopted a method in which the catheter arrangement can be held securely by a force or a pinching means of no more than a degree of their inner diameter being not deformed although without the provision of the stopper (87).

Figure 13:
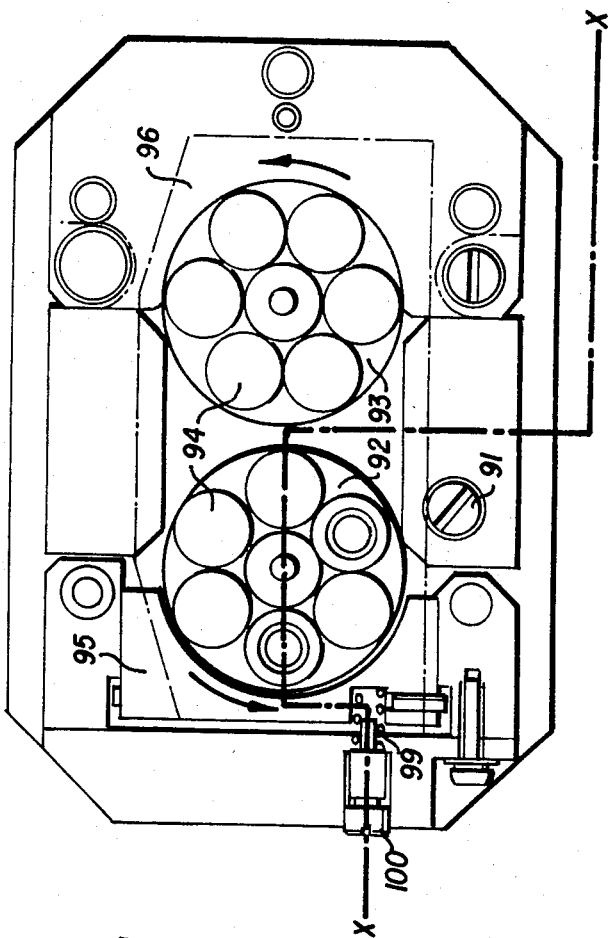
FIG. 13 is a plan view showing an example of the tube pumps for use in the invention.
Figure 14:
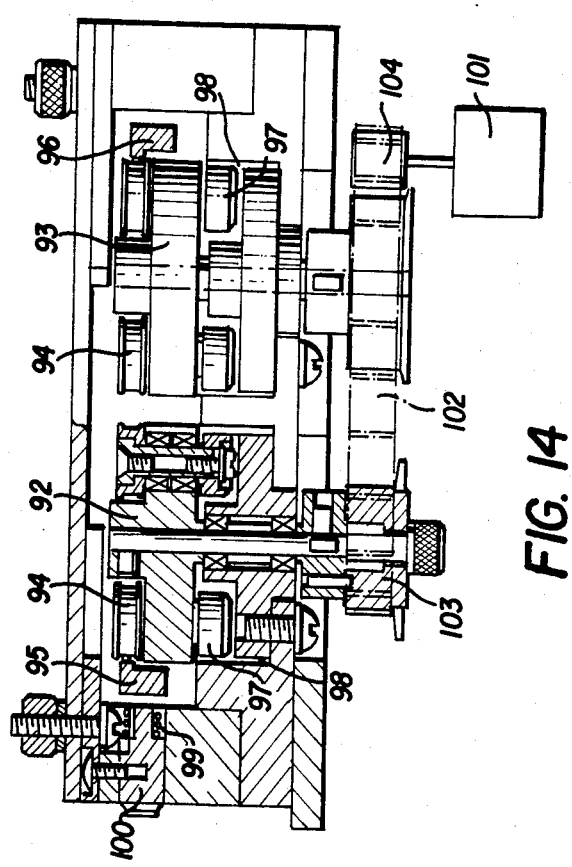
FIG. 14 is a sectional view taken substantially along the lines X—X in FIG. 13.

Next, in each of the rotors (92),(93) of the tube pump (9), six (6) rollers (94) are arranged concentrically. By the rotation of each of the rotors (92),(93), the portion of the tube being restrained by each of the pump head (95),(96) is drawn and at the same time the liquid start being conveyed. If the six rollers (94) each is made to rotate on their own axis in accordance with the rotation of each of the rotors (92),(93) by the planet mechanism composed of the gear (97) united with the rollers in a body and the internal gear (98) (in this case, it will do well if the diameter of the roller (94) is made equal in size to the diameter of the gear (97)), there is no fear of the tube being not dragged in the rotating direction of the rotor, as a result enabling the life to be prolonged and to lessen the pulsation. As for the pump head (95),(96), they each are encouraged toward the rollers (94) by the springs (99),(99), respectively, as shown in FIGS. 13 and 14, and are adapted to draw the tubes always uniformly while pinching them between themselves and the rollers. By the way, the reference numeral (100) indicates an adjusting screw.

On the other hand, the anticoagulant (12) is conveyed from the anticoagulant container (19) through the bottle needle (84) and the first catheter arrangement (81) by the pumping action into the interior of the canula (11a) whose front part is being detained in the vein (V), while the sample liquid (16) as the mixed liquid of the blood (BL) with the anticoagulant (12) is conveyed in the same way by the pumping action through the small tube (85), the second catheter arrangement (82), and the connecting pipe (86) into the sample liquid cup (15). Incidentally, the reference numeral (191) in FIG. 1 indicates an air-introducing needle to be introduced into the anticoagulant container (19). The quantity of anticoagulant (12) infused is determined by the use of the number of revolution of the rotor (92) and the inner diameter of the tube at the tube pump-fitting part (81a), while the quantity of diluted sample liquid (16) sucked is established on the basis of the number of revolutions of the rotor (93) and the inner diameter of the tube at the tube pump-fitting part (82a). However, since the respective inner diameters of both the tube pump-fitting parts can be regarded as the same, as mentioned before, each of the quantities of liquid conveyed comes to be proportional only to the respective numbers of revolutions of both the rotors (92),(93). In this example, the rotors (92),(93) each are designed to be drivable connectedly by means of a motor (101) having the stable revolution such as a single-pulse motor, a timing belt (102) and the like, and consequently it becomes possible to obtain the respective optional speeds of revolution by changing the respective diameters of the pulleys (103),(104) attached to the rotors (92), (93). Consequently, it is also possible to acquire the desired dilution ratio at will, thereby becoming practicable to perform the satisfactory blood-drawing of a hight dilution ratio at which the quantity of anticoagulant infused and the quantity of sample liquid sucked approximate each other. In this case, it does not matter if motors to be used here are 2 in number and are adjusted respectively as to the number revolution. In addition, since a portion of the second catheter arrangement for used in conveying the sample liquid functions in the character of a pump tube, all length of that arrangement from the small tube (85) to the connecting pipe (86) is able to be regarded as having a substantially uniform inner diameter. It follows from this that the linear velocity of the stream (travelling distance per unit time) is invariable even if the inner diameter of that arrangement (82) varies at the time of exchanging the catheter (8). In consequence, so long as the length of the second catheter arrangement (82) does not vary, the time required for the sample liquid (16) to start from the canula (11a) and flow into the sample liquid cup (15) is also invariable, so that it becomes possible to omit the calculation of the time lag which is conducted heretofore at every time of exchanging the catheter. Further, since the tube from the anticoagulant container (19) up to the canula (11a) and from the canula (11a) up to the connecting pipe (86) is made of a single and seamless tube, foreign matters are hard to deposit there and there is hardly possibility of the arrangement getting clogged during the measurement. What is more, this improved double-current catheter (8), in which some portions of the catheter arrangements (81),(82) serve both as substitutes for conventional pump tubes, are simple in construction, as a result it is possible to do the exchanging job very easily and quickly.

In the above example, silicone tubes are used for the catheter arrangements, but in addition to that, it is permissible to make free use of something suitable to materials for tube pumps such as Tigon tube and others. Besides, it is also possible to make such modifications as by, for example, inserting the first catheter arrangement (81) directly into the anticoagulant container (19) with the bottle needle (84) omitted and by using for the tube pump (9) the two ones which have the 1-channel discharge heads and are arranged in a row.

As clearly understood from the above, the device for automatically and continuously measuring the value of the blood sugar which is made through putting the present invention to practical use, wherein the sampling of the sample liquid, the standard liquid, and the base liquid is repeatedly made in order in the state of flowing the sample liquid continuously into the sample liquid cup, all of these three liquids flow through one and the same channel, and in this way the measurement of the value of the blood sugar is performed while correcting successively the measured value of the sample liquid with the aid of the measured values of the standard liquid and the base liquid which are approximate to each other, which device enables the value of the blood sugar and its pattern of fluctuation to be measured automatically, continuously and accurately without being affected by the change in the state of stream peculiar to the tube pumps. However, this invention is not limited to the above-mentioned described example. It goes without saying that it can be widely applied to various uses, for example, to the measurement of the other constituent parts than the blood sugar.

In conclusion, on the basis of the design of the present invention, there is adopted the improved double-current catheter which uses a single and continuous tube provided in the blood-drawing section in such a manner as to make it serve both as the catheter arrangement and as the pump tube, and that the first and second catheter arrangements are laid on the respective tube pump heads so as to be directly drawn by the latter. The invention makes a great contribution to the measurement of the constituent parts of the blood in combination with the aforementioned measuring system.

What is claimed is:

1. A device for automatically and continously measuring constituent parts of blood, said constituent parts being continuously drawn from the blood by means of a catheter inserted in a vein, comprising:

blood drawing means for drawing blood;

a tube pump coupled to said blood drawing means;

sample liquid cup means for holding a sample liquid received from said blood drawing means by said tube drawing pump;

standard liquid cup means for holding a standard liquid;

base liquid cup for receiving a base liquid;

sensor means for sensing said constituent part;

sensor means correction means responsive to said standard liquid and said base liquid for correcting said sensor means;

sampling means comprising a single sampling nozzle and nozzle tube for withdrawing said sample liquid, standard and base liquid from their respective cups in a predetermined order, said sampling means further comprising means for separating said withdrawn sample, standard and base liquids with air;

manifold means for receiving said separated standard liquid, base liquid and sample liquid, and for diluting them at an equal rate by the use of a buffer solution, and for interposing a layer of air between said diluted sample, base and standard liquid, and for providing the diluted and separated sample, standard and base liquid as respective measuring liquids; and operation control means coupled to said sensor means for receiving successive signals, in order therefrom, and for correcting said sensor output signals of said sample liquid according to said standard liquid and said base liquid, and for further displaying the value of said constituent part, and further for controlling the operation of said sampling device.

2. A device for automatically and continuously measuring the constituent parts of the blood as set forth in claim 1, wherein said sampling device further comprises a nozzle-holding arm having a front end part supporting said nozzle vertically at said front end part, said nozzle tube connects said nozzle to a tube pump means for sampling use, and a nozzle-holding arm driving mechanism making a front end part of said nozzle-holding arm move back and forth tracing a circular arc, wherein said base liquid cup is fixed fast under either the front end part or a rear end part of said nozzle-holding arm, while said sample liquid cup and said standard liquid cup take positions by turns under another end part of said arm opposingly to said base liquid cup.

3. A device for automatically and continuously measuring the constituent part of the blood as set forth in claim 1 or 2, wherein said catheter is a double-current catheter having a first catheter means for introducing an anticoagulant into a canula and a second catheter means for sucking and taking-out a mixed liquid of the blood and said anticoagulant out of said canula.

4. A device for automatically and continuously measuring the constituent part of the blood as set forth in claim 3, further comprising an anticoagulant container for containing said anticoagulant wherein said first catheter means is formed of a single and continous tube coupled at an end to sad anticoagulant container and said second catheter means is made of a single and continuous tube connected at an end part to said sample liquid cup, wherein said tube pump comprises first and second tube pumps said first catheter means and said second catheter means are coupled to a first tube pump and a second tube pump, respectively, whereby the conveyance of liquids is effectuated by said first tube pump or said second tube pump, respectively.

5. A device for automatically and continuously measuring the constituent part of the blood as set forth in claim 4, further including a bottle needle wherein said first catheter means is coupled at its end part to said bottle needle, while said second catheter means is coupled at its end part to a connecting pipe.

6. The product according to claim 5 wherein said first and second catheter means have substantially identical interior diameters.

* * * * *